United States Patent
Girard et al.

(10) Patent No.: US 10,816,628 B2
(45) Date of Patent: Oct. 27, 2020

(54) METHOD FOR ENHANCING THE IHMT SENSITIVITY OF STEADY-STATE GRADIENT ECHO ACQUISITIONS IN AN MRI SYSTEM

(71) Applicants: UNIVERSITE D'AIX-MARSEILLE, Marseilles (FR); CENTRE NATIONAL DE LA RECHERCHE SCIENTIFIQUE, Paris (FR)

(72) Inventors: Olivier Maciej Girard, Marseilles (FR); Guillaume Didier David Duhamel, Marseilles (FR); Samira Mchinda, Marseilles (FR); Valentin Hugo Jonas Prevost, Saint Bonnet (FR)

(73) Assignees: UNIVERSITE D'AIX-MARSEILLE, Marseilles (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/095,251

(22) PCT Filed: Mar. 23, 2017

(86) PCT No.: PCT/EP2017/056978
§ 371 (c)(1),
(2) Date: Oct. 19, 2018

(87) PCT Pub. No.: WO2017/182229
PCT Pub. Date: Oct. 26, 2017

(65) Prior Publication Data
US 2019/0137588 A1 May 9, 2019

(30) Foreign Application Priority Data

Apr. 19, 2016 (EP) .................................. 16166049

(51) Int. Cl.
| | | |
|---|---|---|
| G01R 33/56 | (2006.01) | |
| G01R 33/561 | (2006.01) | |
| A61B 5/00 | (2006.01) | |
| A61B 5/055 | (2006.01) | |
| G06T 7/00 | (2017.01) | |

(52) U.S. Cl.
CPC ........ *G01R 33/5605* (2013.01); *A61B 5/0042* (2013.01); *A61B 5/055* (2013.01);
(Continued)

(58) Field of Classification Search
CPC .................................................. G01R 33/5605
(Continued)

(56) References Cited

U.S. PATENT DOCUMENTS

| | | | |
|---|---|---|---|
| 9,392,957 B1 * | 7/2016 | Halpern | G01R 33/60 |
| 2017/0261584 A1 * | 9/2017 | James | A61B 5/055 |
| 2019/0101603 A1 * | 4/2019 | Zhang | G01R 33/246 |

OTHER PUBLICATIONS

Varma et al., "Assessing and Reducing the B1 Dependence of Inhomogeneous Magnetization Transfer," Proceedings of the International society for Magnetic Resonance in Medicine, May 10-16, 2014, p. 3334.

(Continued)

*Primary Examiner* — Reena Aurora
(74) *Attorney, Agent, or Firm* — Oliff PLC

(57) ABSTRACT

A method for producing an MRI image includes the steps of acquiring lines of a volume under analysis using a steady-state gradient echo sequence in successive repetition times (TR); and applying an inhomogeneous magnetization transfer (ihMT) pre-saturation module ($T_{MT}$) in each repetition time. The duration of the repetition times is greater than 20 milliseconds.

12 Claims, 3 Drawing Sheets

(52) U.S. Cl.
CPC ........ *A61B 5/7203* (2013.01); *G01R 33/5607* (2013.01); *G01R 33/5613* (2013.01); *G06T 7/0012* (2013.01); *A61B 2576/026* (2013.01); *G06T 2207/10088* (2013.01)

(58) Field of Classification Search
USPC .......................................................... 324/309
See application file for complete search history.

(56) References Cited

OTHER PUBLICATIONS

Jones et al., "In Vivo Three-Dimensional Whole-Brain Pulsed Steady-State Chemical Exchange Saturation Transfer at 7 T," Magnetic Resonance in Medicine, 2012, vol. 67, pp. 1579-1589.

Girard et al., "Whole Brain inhomogeneous MT using an ihMT prepared 3D GRE sequence at 1.5T," Proceedings of the International Society for Magnetic Resonance in Medicine, May 30-Jun. 5, 2015, p. 3356.

Dai et al., "Magnetization Transfer Prepared Gradient Echo MRI for CEST Imaging," PLOS One, Nov. 2014, vol. 9, No. 11, e112219, pp. 1-7.

Girard et al., "Theoretical and Experimental Optimization of a 3D Steady-State Inhomogeneous Magnetization Transfer (ihMT) Gradient Echo Sequence: Boosting the ihMT Sensitivity with Sparse Energy Deposition," Proceedings of the International Society for Magnetic Resonance in Medicine, May 7-13, 2016, p. 2892.

Jun. 29, 2017 International Search Report issued in International Patent Application No. PCT/EP2017/056978.

Jun. 29, 2017 Written Opinion of the International Searching Authority issued in International Patent Application No. PCT/EP2017/056978.

* cited by examiner

Fig 1
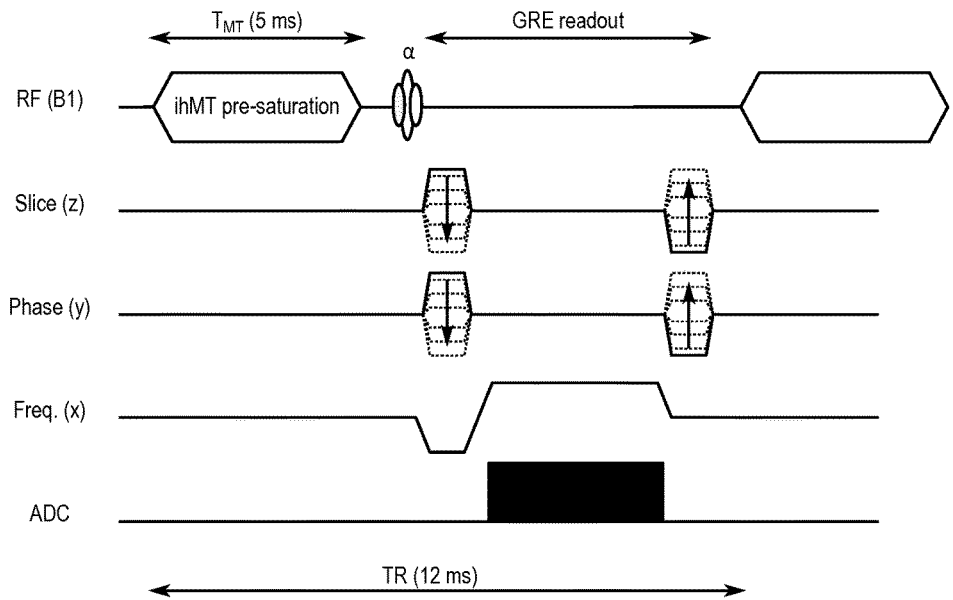
Fig 2
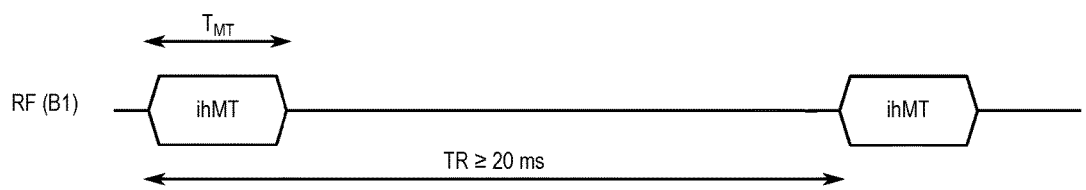
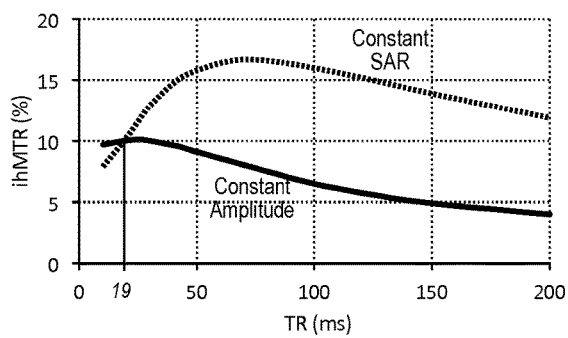
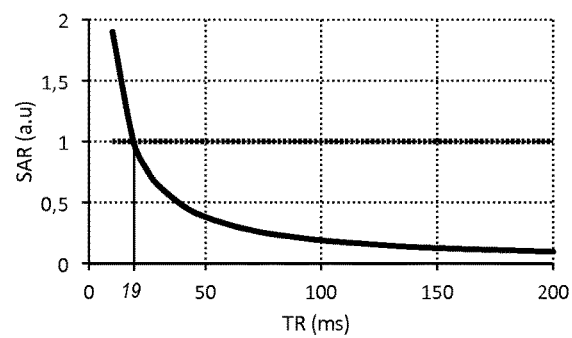
Fig 3A
Fig 3B

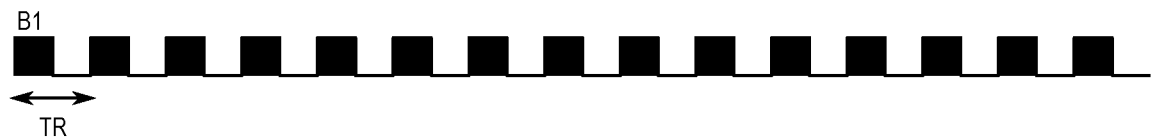
Fig 7A (Distributed RF energy)
Fig 7B (Concentrated RF energy)
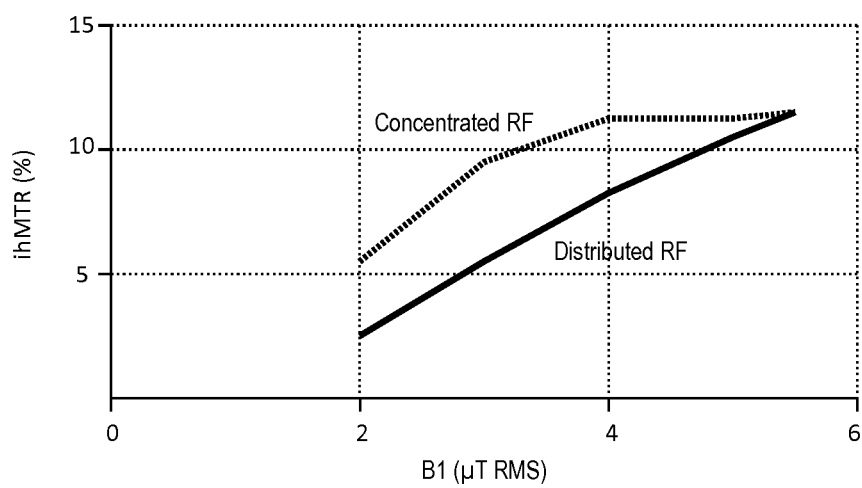
Fig 8

METHOD FOR ENHANCING THE IHMT SENSITIVITY OF STEADY-STATE GRADIENT ECHO ACQUISITIONS IN AN MRI SYSTEM

FIELD

The invention relates to Magnetic Resonance Imaging (MRI), in particular to central nervous system imaging using inhomogeneous magnetization transfer (ihMT) techniques.

BACKGROUND

Single-shot MRI techniques are designed to acquire a volume under analysis slice by slice. The slices are acquired in successive intervals called repetition times TR. Such techniques typically use the whole available longitudinal magnetization M0 in each repetition time, by tipping it by 90° into the transverse plane prior to the signal readout. In that sense magnetization measurement is destructive, whereby a certain time is needed for the longitudinal magnetization to regenerate before the next readout. The repetition time TR is adjusted based on the magnetization regeneration time to allow significant recovery, leading to repetition times of the order of a few seconds.

In contrast, steady-state gradient echo imaging techniques only tip the magnetization by a few degrees towards the transverse plane at each readout, whereby the magnetization is only slightly attenuated each time and recovers partially between radio frequency pulses applied in each repetition time. This procedure allows the magnetization to converge and be maintained at a steady state after a certain number of repetition times. These techniques use significantly shorter repetition times, in the order of ten milliseconds, and are thus more suitable to three dimensional imaging, where a volume may be acquired by individual lines in an arbitrary sequence in successive repetition times.

FIG. 1 is a time diagram illustrating a steady-state gradient echo imaging sequence applied to inhomogeneous magnetization transfer (ihMT), as disclosed, for example, in ["3D Acquisition of the Inhomogeneous Magnetization Transfer Effect for Greater White Matter Contrast", Gopal Varma et al., Proceedings of the 21$^{st}$ Annual Meeting of the International Society for Magnetic Resonance in Medicine (ISMRM), April 2013].

Each repetition time TR of the sequence starts with an ihMT pre-saturation module lasting a time $T_{MT}$. Four different pre-saturation modules are used sequentially. In the first and third repetition times, trapezoidal radiofrequency pulses are applied, having respective frequency offsets of +5 KHz and −5 KHz. In the second and fourth repetition times, an on-resonance cosine modulated trapezoidal pulse is applied such that both +5 KHz and −5 KHz frequency bands are excited simultaneously.

The pre-saturation module is usually followed by a gradient echo (GRE) readout module, which begins with an on-resonance excitation pulse α, then followed by a combination of three gradient coil control signals used for spatial encoding, typically named Slice, Phase and Frequency.

The Slice signal selects a z-coordinate, i.e. a plane perpendicular to the longitudinal magnetic field B0. The selection is operated through the amplitude of a gradient pulse. As illustrated by an arrow, the pulse amplitude may vary between a positive maximum value and a negative symmetrical value to scan all possible z-positions. A similar description applies for the Phase dimension in FIG. 1.

Usually, there is insufficient time within the repetition time TR to readout a significant portion of a volume under analysis, for instance all the lines or y-coordinates in a slice. Only one line at a time is read out here. The current line is selected by a corresponding amplitude of a pulse of the Phase signal, as shown.

Finally, the Frequency signal waveform is configured to extract all x-positions in the selected line, in the form of an echo signal. The echo signal is sampled, as shown by a black rectangle ADC, while the Frequency signal is at a high level. After the echo signal has been sampled, each of the Slice and Phase signals may be "rewound" by applying a gradient pulse of opposite amplitude than the initial selection pulse, as illustrated.

Exemplary durations of the pre-saturation module $T_{MT}$ and of the repetition time TR, respectively 5 and 12 milliseconds, are indicated in parenthesis and correspond to values suggested in the above ISMRM paper by Varma et al.

A useful contrast for examining central nervous system tissue by MRI is the ihMT ratio, denoted ihMTR and expressed in percent. This contrast has a rather low sensitivity, producing values reaching 10% in the best cases. Any technique for increasing the sensitivity is highly desirable.

SUMMARY

A general method is provided herein for increasing the ihMTR contrast sensitivity, comprising the steps of acquiring lines of a volume under analysis using a steady-state gradient echo sequence in successive repetition times; and applying an inhomogeneous magnetization transfer pre-saturation module in each repetition time. The duration of the repetition times is greater than 20 milliseconds, preferably greater than 30 milliseconds.

The duration of the repetition times may in addition be at least four times greater than the duration of the pre-saturation modules.

The radiofrequency intensity applied in the pre-saturation modules may be adjusted to maintain a specific absorption rate reference level based on the actual value of the repetition time and on the amplitude of a static magnetic field applied to the volume under analysis.

The repetition time may be selected from a range above 70 ms, where a produced contrast value is substantially insensitive to variations of the radio frequency intensity over space (so called RF non-uniformity), which are typically associated with RF propagation effects, especially at higher magnetic field strengths (i.e. 3T or above).

Multiple lines may be acquired within each repetition time.

The duration of the pre-saturation modules may be comprised between 8 and 16 milliseconds, and is preferably substantially equal to 12 milliseconds.

Each pre-saturation module may include equally spaced Hann-shaped radiofrequency pulses, preferably twelve radiofrequency pulses spaced at a pitch of one millisecond.

Each pre-saturation module may include radiofrequency pulses spaced at a pitch greater than the dipolar order relaxation time of a tissue to filter in the image, for instance greater than 2.5 milliseconds, whereby muscle tissue is filtered in the image.

BRIEF DESCRIPTION OF DRAWINGS

Other advantages and features will become more clearly apparent from the following description of particular embodiments of the invention provided for exemplary purposes only and represented in the appended drawings, in which:

FIG. 1, previously described, is a time diagram illustrating a conventional ihMT-prepared steady-state gradient echo imaging sequence;

FIG. 2 is a time diagram illustrating a steady-state gradient echo imaging sequence that enhances the sensitivity of ihMTR contrast;

FIGS. 3A and 3B are simulation result graphs showing sensitivity enhancements obtained using the sequence of FIG. 2;

FIGS. 7A and 7B schematically illustrate two imaging sequences using a same average RF power conveyed in the pre-saturation modules when integrated over time, but with different repetition time values; and FIG. 8 is a graph showing ihMTR contrast variations as a function of the average RF power for sequences using different peak amplitudes in the pre-saturation modules, such as shown in FIGS. 7A and 7B.

DESCRIPTION OF EMBODIMENTS

Figure 4:
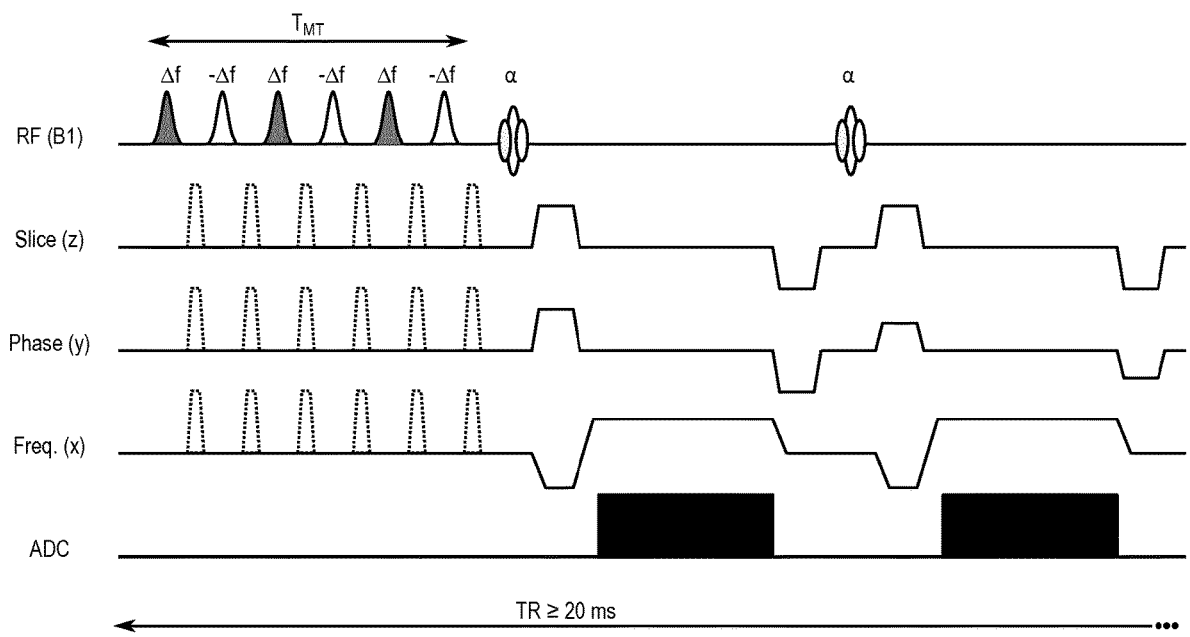
FIG. 4 is a time diagram partially illustrating a steady-state gradient echo imaging sequence that may be used for reducing acquisition times when implementing the sequence of FIG. 2.

In inhomogeneous magnetization transfer (ihMT) steady-state gradient echo sequences for MRI, such as illustrated in FIG. 1, it is customary to make the repetition time TR as short as possible. For this purpose, the repetition time is chosen as close as possible by excess to the pre-saturation module duration $T_{MT}$, plus the duration of a single line readout sequence. A first reason for this choice is that shorter repetition times will reduce the total acquisition time, hence reducing motion sensitivity. A second reason originates from the ihMT model used for characterizing semisolid matter.

Semisolid matter, such as white and gray matter, is modeled by a pool including two interconnected compartments, called the dipolar order β and the semisolid Zeeman order $M_{ZB}$. It is sought to measure the dipolar order, but it cannot be measured directly. The ihMT techniques are designed to transfer magnetization representing the dipolar order to a liquid proton pool formed by a compartment called the liquid Zeeman order $M_{ZA}$, where the value can be acquired directly through MRI.

The dipolar order has a short life time or relaxation time (T1D) after build-up by each pre-saturation module, in the order of 6-10 milliseconds for grey and white matter. It is believed that pre-saturation modules should be repeated close enough after each other to regenerate the dipolar order before it fully decays, explaining why repetition times should be as short as possible.

The inventors have doubted this belief and propose in contrast to lengthen the repetition times. Indeed, the inventors noted that ihMT techniques do not directly measure the dipolar order, but its effect as transferred to the liquid pool. The transferred effect actually has a much longer relaxation time, in the order of one second, theoretically meaning that repetition times as long as one second may be used with little loss of sensitivity.

Simulations and experiments conducted by the inventors prove that longer repetition times may even increase sensitivity, as shown hereafter.

FIG. 2 is a time diagram illustrating a steady-state gradient echo imaging sequence that thus enhances the sensitivity of ihMTR contrast. This diagram is based on the diagram of FIG. 1, wherein only the differing elements have been shown. The inventors have found that repetition times TR longer than 20 milliseconds may improve sensitivity of ihMT signals.

Repetition times used conventionally in ihMT steady-state gradient echo sequences have been below 20 milliseconds, for instance 12 milliseconds in the previously mentioned paper by Varma. The paper ["Whole Brain inhomogeneous MT using an ihMT prepared 3D GRE sequence at 1.5T", Olivier Girard et al., ISMRM 2015] suggests a repetition time of 19 milliseconds.

FIGS. 3A and 3B are simulation result graphs showing sensitivity enhancements obtained with repetition times TR varying between 10 and 200 milliseconds.

All simulations and experiments herein are conducted with RF energy intensities derived from experiments performed at a static magnetic field of intensity B0=1.5 T. The examined tissue is a white matter bundle named the pyramidal tract, denoted PT, which is the tissue that provides the highest ihMTR values, near 10% with conventional methods. The pre-saturation modules include RF pulse trains, rather than modulated pulses.

In FIG. 3A, the y-axis expresses the ihMTR contrast or sensitivity in percent. The solid-line curve represents the evolution of the sensitivity where only the repetition time is changed, i.e. the pre-saturation modules used throughout the simulation have the same characteristics, in particular constant amplitude. The pre-saturation modules are in fact such as disclosed in the above ISMRM paper by Girard et al., i.e. six Hann-shaped pulses spaced at a pitch of 1 millisecond, each having a 0.5-millisecond width.

The radio frequency pulse amplitude B1 is set in the simulations so that the root-mean-square (RMS) value achieves 5.4 µT over a repetition time of 19 milliseconds. Thus the RMS value decreases when TR increases above 19 milliseconds, and increases when TR decreases below 19 milliseconds.

It can be noted that the sensitivity does not decrease, but even increases to a maximum above 10% for TR between 20 and 30 milliseconds, thus a higher value than achieved with the conventional range of repetition times below 20 milliseconds.

It is known that sensitivity increases to a certain extent with the energy transferred by the pre-saturation modules. In fact, the transmissible energy is limited to an authorized Specific Absorption Rate (SAR) that ensures patient safety. The RMS value of 5.4 µT mentioned above, achieved for TR=19 ms, corresponds to an exemplary SAR reference level.

FIG. 3B illustrates variations of the SAR with the repetition time. The values on the y-axis are normalized SAR factors, i.e. ratios of the actual SAR values to a reference SAR level obtained for an RMS B1 value of 5.4 µT and for TR=19 ms. The solid-line curve corresponds to the constant amplitude curve of FIG. 3A. The SAR decreases inversely proportionally to the repetition time. Whereas the reference SAR (1.0) is reached at TR=19 ms, producing an ihMTR value of 10% (in FIG. 3A), the SAR is only at 0.65 for TR=30 ms while producing the same ihMTR value. This available SAR margin leaves room for two types of enhancements that may be applied individually or in combination.

First, the energy in the pre-saturation modules may be increased, expending the available SAR margin to seek higher sensitivity.

Second, the longitudinal magnetic field B0 may be increased, which also expends the SAR margin, while maintaining the ihMTR sensitivity, but offering higher signal to noise ratio.

The dotted curves in FIGS. 3A and 3B, labeled "Constant SAR", correspond to the first option. The pulse amplitude B1 of the pre-saturation modules increases with TR so that the RMS value of the pulses is maintained constant. As shown in FIG. 3B, the SAR thus stays constant at the reference level over the TR range.

As shown in FIG. 3B, the sensitivity increases rapidly as TR increases beyond 20 ms, reaching heretofore-unattained values for TR beyond 30 ms. A maximum close to 17% is reached for TR between 60 and 80 ms.

Increasing the repetition time TR without further measures obviously increases the total acquisition time. With conventional short repetition times, only one line could be acquired each time. However, with durations as long as 20 ms and above, there is sufficient time to acquire multiple lines within each repetition time.

FIG. 4 is a time diagram partially illustrating a steady-state gradient echo imaging sequence where multiple lines are acquired within one repetition time TR. The diagram is similar to that of FIG. 1 for the pre-saturation phase $T_{MT}$ and the acquisition of the first line.

The pre-saturation module has been illustrated in more detail and corresponds to that used in the previously mentioned ISMRM paper by Girard. The pre-saturation module is one among four possible modules, each including a train of six RF pulses. The pulses may be Hann-shaped, have a 0.5-millisecond width and be spaced at a pitch of 1 ms. The shown module, as an example, includes pulses with alternating frequency offsets ±Δf, for instance ±7 KHz, starting with a pulse of positive offset. The other modules have pulses with different sequences of frequency offsets.

As shown by lobes in dotted lines, one or several of the Slice, Phase and Frequency signals may convey so-called "spoiler gradient" pulses interleaved in time with the radiofrequency pulses Δf, serving the purpose of canceling residual transversal signals.

After the pre-saturation module, several lines may be read out, filling the available time left up to the end of the repetition time TR. Each line may be read out in a sequence similar to that for reading the single line in FIG. 1, i.e. starting with an excitation pulse α, followed by an amplitude pulse in each of the Slice and Phase signals, and a pattern of the Frequency signal. Each readout sequence may end with a rewind pulse in each of the Slice and Phase signals.

The amplitudes of the Phase and Slice pulses vary from one readout to the next, as illustrated, to describe a desired line-acquisition sequence or trajectory.

With this procedure, the use of longer repetition times does not increase the total acquisition time. In fact, the total acquisition time may even be reduced, since one pre-saturation module is used for the readout of multiple lines, whereas in a conventional sequence such as in FIG. 1, one pre-saturation module is used for each line.

Pre-saturation modules have conventionally been short, in the order of 5 milliseconds, each using either a single cosine modulated trapezoidal pulse, or a train of six frequency offset pulses.

Figure 5A:
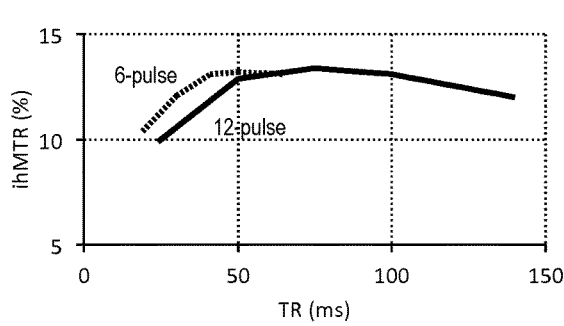
FIGS. 5A and 5B are experimental result graphs showing sensitivity enhancements obtained using different numbers of pulses in the pre-saturation module.
Figure 5B:
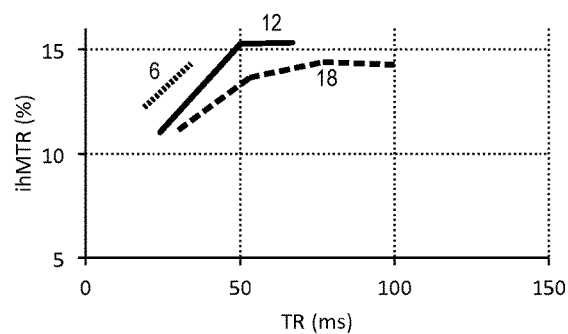

FIGS. 5A and 5B are ihMTR versus TR graphs of experimental results based on varying pre-saturation module durations. The experiments were carried out with pulse trains of varying number of pulses, where the pulses have the same width (0.5 ms) and are spaced by the same pitch (1 ms). The pulse amplitudes are variable to achieve a constant RMS B1 value of 5.4 µT. Similar results may be expected with cosine-modulated pulses of varying widths.

In practice, to achieve an RMS B1 value of 5.4 µT without exceeding the reference SAR, an additional optimization may be implemented, a so-called partial-Fourier boost technique. Such a technique is based on the fact that the readout signals as acquired happen to represent a Fourier transform of the volume under analysis. In a spatial Fourier transform, the most representative data is concentrated in the center. Neglecting the peripheral data to a certain extent in the Fourier domain produces satisfactory images after an inverse transform.

The partial-Fourier boost technique applies RF energy only in acquiring the central lines of the volume under analysis. These central lines are acquired first, and the remaining, peripheral lines are acquired subsequently using zero-amplitude pulses in the pre-saturation modules, thereby reducing the SAR.

In the examples shown in FIGS. 5A and 5B the partial-Fourier boost technique is applied to the 50% center-most lines, in both Phase (y) and Slice (z) dimensions, using a center-out square spiral acquisition trajectory.

FIG. 5A explores Tukey-shaped pulses, for sake of completeness. Indeed, the pulses are conventionally Hann-shaped. Tukey-shaped pulses are broader and thus convey more energy.

The dotted-line curve corresponds to six pulses and the solid-line curve to twelve pulses. The six-pulse curve exhibits a maximum for TR near 50 ms, whereas the twelve-pulse curve exhibits a slightly larger maximum for TR near 75 ms. Thus the choice of twelve pulses rather than six results in a perceptible enhancement of the sensitivity.

Bearing in mind the inaccuracies due to the small number of experimental points, it appears that the maximum of the twelve-pulse curve lies approximately twice as far in the TR-axis than the maximum of the six-pulse curve. Also, the twelve-pulse curve appears to have a wider dome shape than the six-pulse curve, by a factor 2. The width of the dome and the position of the maximum thus correlate to the number of pulses, or more generally to the length $T_{MT}$ of the pre-saturation module.

These findings lead to a generic rule, independent of the pre-saturation module length, for selecting a good repetition time TR. It appears from FIG. 5A that a TR approximately equal to $7T_{MT}$ provides good results. More generally, TR may be a multiple of $T_{MT}$, the multiplication factor depending on the configuration of the pre-saturation modules, as discussed below.

FIG. 5B explores the more conventional Hann-shaped pulses and shows curves obtained for 6-, 12- and 18-pulse pre-saturation modules.

The 6-pulse curve was obtained in experimental conditions corresponding to the simulation conditions of FIG. 3A (dotted-line curve). The available experimental points are above the simulated results.

The 12-pulse curve reaches a maximum value for TR≥50 ms, while the 18-pulse curve reaches a maximum value for TR near 75 ms.

The 12-pulse curve reaches the highest values achieved in the experiments reported herein, i.e. above 15%. FIG. 3B thus shows that a significant improvement is achieved with around 12 pulses rather than 6 or 18. This is also true for Tukey-shaped pulses (FIG. 5A). It is thus foreseeable that 8 to 16 pulses may achieve better sensitivity results than the traditional 6 pulses.

The discussion in number of pulses above may be translated in terms of durations for other types of pre-saturation modules. Since the discussed pulses have a spacing pitch of 1 ms and a width of 0.5 ms, choosing a number of pulses between 8 to 16 translates to choosing a pre-saturation module duration $T_{MT}$ between 7.5 and 15.5 milliseconds, thus approximately 8 and 16 milliseconds. Similarly, choosing 12 pulses translates to choosing approximately 12-millisecond pre-saturation modules.

It appears from FIGS. 5A and 5B that the pulse-shape has an influence on the position of the maximum. In FIG. 5B, based on the 18-pulse curve that has the most experimental points, the optimal duty ratio $T_{MT}/TR$ appears to be around ¼ instead of ⅐ in FIG. 5A. In fact the position of the maximum varies with the energy distribution within the pre-saturation modules. For instance, Tukey-shaped pulses (FIG. 5A) convey the same energy in broader but lower amplitude pulses than Hann-shaped pulses (FIG. 5B), causing the dome of the ihMTR curve to be broader and the summit of the dome to be further away.

Whatever configuration is used for the pre-saturation modules, selecting TR greater than 20 ms, preferably greater than 30 ms, and the duty ratio $T_{MT}/TR$ smaller than ¼ will generally provide satisfactory results.

Figure 6:
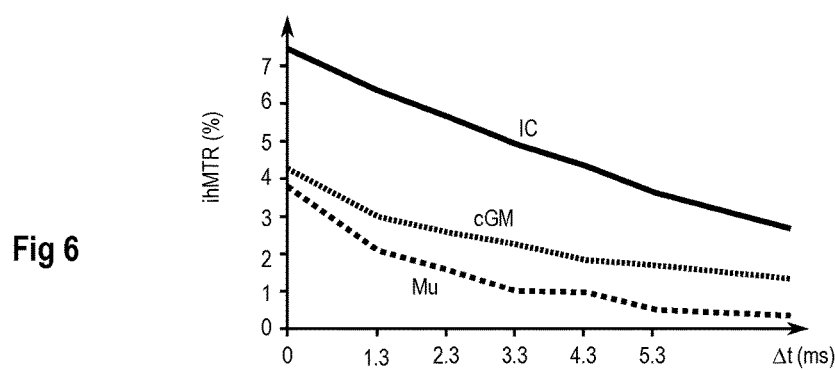
FIG. 6 is a graph illustrating sensitivity variations for tissues with different dipolar order relaxation times as a function of the pulse spacing in the pre-saturation module.

FIG. 6 explores different spacing pitch values Δt for the pulses, here using six Hann-shaped pulses, for three different tissue types (muscle Mu, cortical gray matter cGM, and intra-capsule white matter IC). A Δt of 0 corresponds to a single cosine modulated pulse.

The ihMTR values all decrease with an increase of the pitch. It can be noted that, for short Δt values, the muscle tissue sensitivity Mu starts close to the gray matter sensitivity cGM, whereas the sensitivity Mu decreases faster than the sensitivity cGM. At Δt=2.5 ms, the sensitivity Mu has reached half its initial amplitude. In fact, 2.5 ms is approximately the relaxation time T1D of the dipolar order in muscle tissue.

The general sensitivity decrease with an increase of the pulse spacing is another reason that may have led to the conventional belief that shorter repetition times were better. Indeed the better results achieved with closer spaced radiofrequency pulses could have led to expecting better results with closely spaced pre-saturation modules, which is not true as demonstrated above.

Under conventional conditions (i.e. a Δt of 0 or 1 ms), it may be hard to discriminate gray matter from muscle if both are present in a volume under analysis, since the ihMTR values are close. To better discriminate grey matter under those circumstances, it is proposed to filter the Mu signal by selecting Δt greater than the dipolar order relaxation time of muscle tissue, i.e. 2.5 ms.

More generally, a given choice for the pitch Δt will attenuate and/or filter signals from all tissues having dipolar relaxation times smaller than the pitch.

As previously mentioned, for instance with relation to FIGS. 3A and 3B, it is desirable to choose the magnetic RF pulse amplitude B1 of the pre-saturation modules so that a reference SAR is respected in overall. To achieve this constraint, since the effective width of the pre-saturation modules is typically constant, the RF pulse amplitude may be increased with the used repetition time value TR. This leads to two types of imaging sequences illustrated below, both conveying the same overall magnetic RF energy.

In FIG. 7A, a repetition time TR in a lower range is used, for instance near 20 ms, leading to many low-energy RF pulses (illustrated in black) distributed over a given time interval. Such a sequence will be referred to as a "distributed RF-energy" sequence.

In FIG. 7B, a repetition time TR in a higher range is used, for instance near 100 ms, leading to a few high-energy RF pulses spaced over the given time interval. Such a sequence will be referred to as a "concentrated RF-energy" sequence, because the same energy is conveyed over substantially fewer pulses.

It appears that these two types of sequences, although they convey the same overall RF energy, have different effects on the susceptibility of the ihMTR contrast to undesired variations of the RF-pulse amplitude.

FIG. 8 is a graph showing ihMTR contrast variations as a function of the RMS pulse amplitude for an exemplary distributed RF-energy sequence (bold line) and for an exemplary concentrated RF-energy sequence (dotted line). A repetition time of 24 ms was used for the distributed RF-energy sequence, and a repetition time of 140 ms was used for the concentrated RF-energy sequence. The B1 RMS value of the pulses varies between 2 and 5.5 µT for data acquired at B0=1.5 T.

As shown, the ihMTR contrast varies substantially linearly with the B1 RMS value when a distributed RF-energy sequence is used. When a concentrated RF-energy sequence is used, the ihMTR contrast starts at a higher value and tends to a plateau when B1 RMS reaches approximately 4 µT RMS, in this example.

As a consequence, when using a concentrated RF-energy sequence with sufficient power, the ihMTR contrast becomes insensitive to undesired variations of the pulse amplitude B1.

This property may be used at any magnetic field strength, especially at higher static field strengths (e.g. 3 T or above) to mitigate susceptibility to RF non-uniformity effects. An experiment was conducted at B0=3 T (for which lower B1 RMS powers are typically used), using a nominal B1 RMS value of 2.2 µT and a repetition time of 19 ms (thus a distributed RF-energy sequence). Under these conditions, the average ihMTR contrast of white matter in a sample brain image varied with a slope of 0.059. The slope is here expressed in units of the ihMTR contrast for each percent variation of the nominal B1 RMS value.

Using a repetition time of 260 ms (thus a concentrated RF-energy sequence), in the same conditions, yielded a slope of 0.0035, which is smaller by more than one order of magnitude, and demonstrates a reduced susceptibility to undesired variations of the pulse amplitude B1.

The repetition time threshold that distinguishes a "concentrated" RF-energy sequence, offering the improvements discussed above, from a "distributed" RF-energy sequence depends on several parameters of the specific application, such as the nominal B1 RMS value, the static magnetic field strength B0, the width of the pre-saturation modules, and also the desired ihMTR sensitivity gain. Good results were achieved with a repetition time of 140 ms at B0=1.5 T for B1 RMS>4 µT, and of 260 ms at B0=3 T for B1 RMS around 2.2 µT, in the examples discussed above, but visible improvements may be achieved with repetition times as low as 70 ms in some cases, i.e. the TR value where the best sensitivity gain is achieved (FIG. 3A).

Usually the nominal B1 RMS value will be adjusted with respect to a reference SAR, depending on the static magnetic field strength B0. In such conditions, the desired repetition time may be determined experimentally to achieve a compromise between the sensitivity gain (lower repetition times around 70 ms here) and the immunity to spurious variations of the pulse amplitude B1 (repetition times around 140 ms or above here).

The invention claimed is:

1. A method for producing a Magnetic Resonance Imaging (MRI) image, comprising the following steps:
   acquiring lines of a volume under analysis using a steady-state gradient echo sequence in successive repetition times, wherein a duration of each repetition time is greater than 20 milliseconds; and
   applying an inhomogeneous magnetization transfer pre-saturation module in each repetition time, wherein the pre-saturation modules are configured to achieve a steady-state of magnetization after multiple repetition times.

2. The method of claim 1, wherein the duration of each repetition time is greater than 30 milliseconds.

3. The method of claim 1, wherein the duration of each repetition time is at least four times greater than the duration of a pre-saturation module.

4. The method of claim 1, wherein a radiofrequency intensity applied in the pre-saturation modules is adjusted to maintain a specific absorption rate reference level based on an actual value of the repetition time and on an amplitude of a static magnetic field applied to the volume under analysis.

5. The method of claim 4, wherein the radiofrequency intensity is at least 4 $\mu$T and the repetition time is selected from a range above 70 ms, whereby a produced contrast value is substantially insensitive to variations of the radiofrequency intensity.

6. The method of claim 1, wherein multiple lines are acquired within each repetition time.

7. The method of claim 1, wherein the duration of each pre-saturation module is comprised between 8 and 16 milliseconds.

8. The method of claim 7, wherein the duration of each pre-saturation module is substantially equal to 12 milliseconds.

9. The method of claim 7, wherein each pre-saturation module includes equally spaced Hann-shaped radiofrequency pulses.

10. The method of claim 9, wherein each pre-saturation module includes twelve radiofrequency pulses spaced at a pitch of one millisecond.

11. The method of claim 10, wherein the radiofrequency pulses are spaced at a pitch greater than 2.5 milliseconds.

12. The method of claim 1, wherein each pre-saturation module includes radiofrequency pulses spaced at a pitch greater than a dipolar order relaxation time of a tissue to filter in the image.

* * * * *